United States Patent [19]

Menge et al.

[11] 4,343,735

[45] Aug. 10, 1982

[54] PROCESS FOR THE PURIFICATION OF INTERFERON

[75] Inventors: Ulrich Menge; Michael Morr, both of Brunswick; Maria-Regina Kula; Kristin Anastassiadis, both of Wolfenbüttel, all of Fed. Rep. of Germany

[73] Assignee: Gesellschaft fur Biotechnologische Forschung mbH (GBF), Braunschweig-Stockheim, Fed. Rep. of Germany

[21] Appl. No.: 200,015

[22] Filed: Oct. 23, 1980

[30] Foreign Application Priority Data

Oct. 24, 1979 [DE] Fed. Rep. of Germany ....... 2943016

[51] Int. Cl.$^3$ ..................... C07C 103/52; A61K 45/02
[52] U.S. Cl. .................................. 260/112 R; 424/85
[58] Field of Search ...................... 424/85; 260/112 R; 435/68, 811

[56] References Cited

U.S. PATENT DOCUMENTS 3,144,390 8/1964 Burke ..................................... 424/85
3,256,152 6/1966 Sampson ............................... 424/85

OTHER PUBLICATIONS

Flanagan, S., et al., J. Biol. Chem., vol. 251, pp. 858–865, 1976.
Flanagan, S. et al., J. Biol. Chem., vol. 250, pp. 1484–1489, 1975.
Bridger, P., et al., J. Biol. Chem., vol. 252, pp. 6585–6587, 1977.

*Primary Examiner*—Blondel Hazel
*Attorney, Agent, or Firm*—Hammond & Littell, Weissenberger and Muserlian

[57] ABSTRACT

The invention concerns a process for the purification of interferon, where interferon is purified by partitioning interferon in an aqueous multi-phase system in the presence of ion exchangers that are soluble in this system and that are derivatives of polyethers.

16 Claims, 1 Drawing Figure

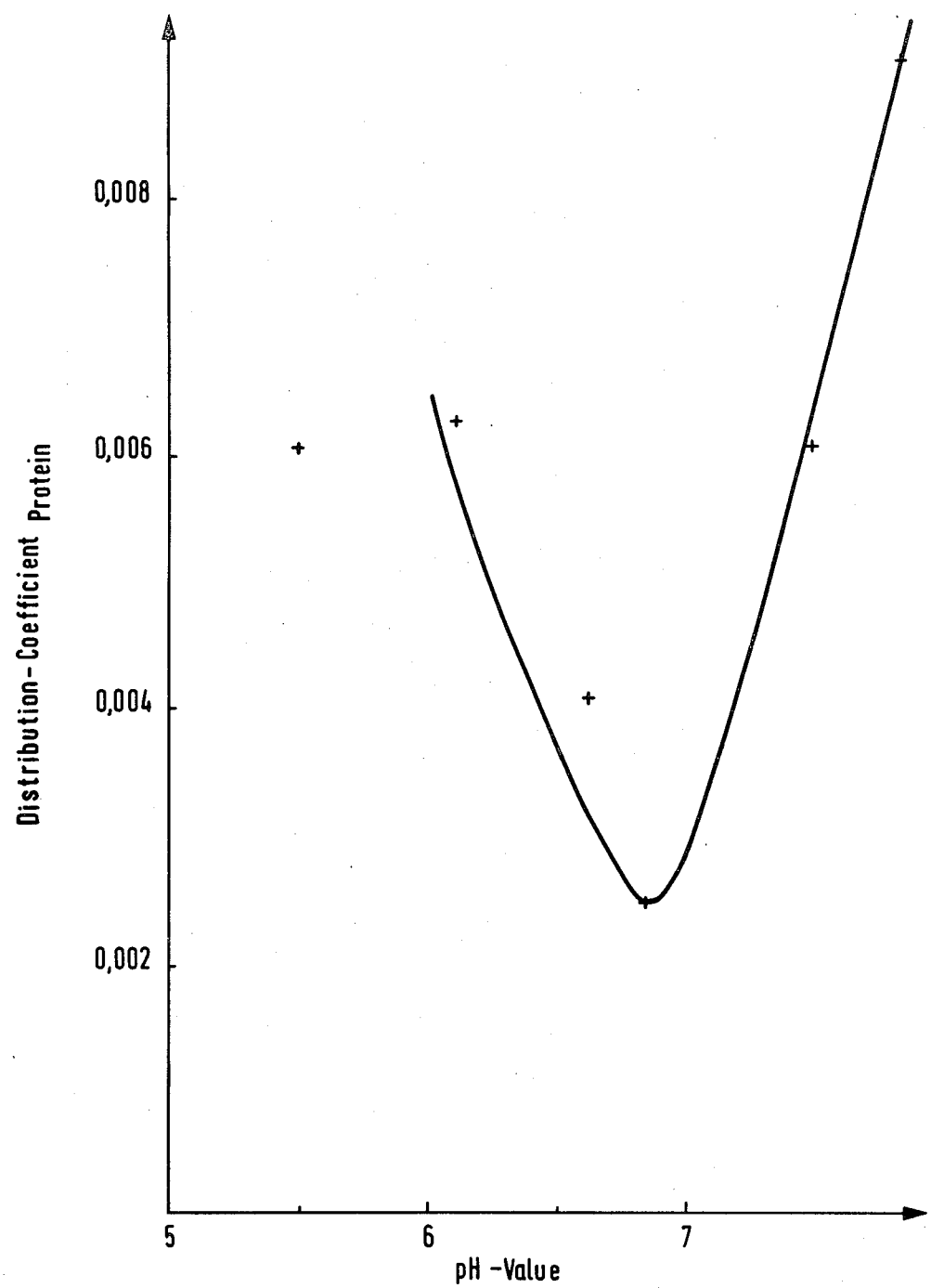

PROCESS FOR THE PURIFICATION OF INTERFERON

The invention relates to a process for the purification of interferon. Interferon is a collective term for certain protein-like substances, such as, for example, described in more detail by S. Kobayashi, Interferon, Kodansha Ltd., Tokyo 1975; D. A. J. Tynell, Interferon and its clinical potential, W. Heinemann Medical Books Ltd., London 1976; Protein, Nucleic Acid and Enzyme, 21 (4) (1976) (publishers: K. Shuppan Co., Ltd.); Vilcek et al., Ann. NY Acad. Sci. (1977) 703–710; Havell et al., J. Gen. Virology, 38 (1977) 51–59; and Knight, Proc. Nat. Acad. Sci., 73 (1976) 520–523. Information on how to obtain it is given, for example in the following U.S. Pat. Nos.: 3,144,390; 3,256,152; 3,265,581; 3,548,053; 3,560,611; 3,629,235; 3,660,564; 3,679,654; 3,699,222; 3,719,754; 3,773,924; 3,775,398; 3,800,035; 3,803,302; 3,843,629; 3,852,423; 3,929,991; 3,931,397; 3,932,617; 3,966,707; 3,970,749; 3,975,344; 3,975,520; 3,980,776; 3,981,991; 4,007,086; 4,017,359; 4,017,600; 4,024,222; 4,024,241; 4,039,656; 4,041,152; 4,049,794; 4,061,538; 4,100,150; 4,124,702; 4,130,641; 4,132,775; 4,140,761; and in German Offenlegungsschrift No. 24 47 781.

In the purification of interferon, the separation of accompanying proteins has hitherto presented difficulties.

According to the invention, a process is now proposed for the purification of interferon, that is characterised in that interferon is partitioned in an aqueous multi-phase system in the presence of ion exchangers that are soluble in this system and that are derivatives of polyethers, for example derivatives of (a) polyalkylene glycols or (b) reaction products of polyhydric alcohols with alkylene oxides.

In the process according to the invention it is surprising that both anion exchangers and also cation exchangers can be used successfully. Partition coefficients of up to 100 or more for interferon and less than 1 for the accompanying proteins can be obtained.

Derivatives of (a) polyalkylene glycols or (b) reaction products of polyhydric alcohols with alkylene oxides, that are ion exchangers soluble in an aqueous multi-phase system, are available to the man skilled in the art. In the manufacture of aqueous multi-phase systems containing soluble ion exchangers of this type, the man skilled in the art has recourse to the known aqueous multi-phase systems containing polyethers or polyether derivatives. In this connection, reference is made, for example, to DE-PS No. 26 39 129; the disclosure of this patent specification together with the literature mentioned therein is included here.

For the process according to the invention, derivatives (a) and/or (b) can be used that have one, two or more C-bonded, preferably terminal, radicals —$S_{0-1}$—Z, wherein Z is a radical that imparts to the derivatives the characteristics of Brønsted acids, Brønsted bases or Lewis bases having a pK value of from 2 to 10;

S—Z is a radical from the following group:
—NH—$(CH_2)_{1-14}$—Z,
—O—$(CH_2)_{1-14}$—Z,
—NH—CO—$(CH_2)_{1-14}$—Z,
—NH—$(CH_2)_{1-14}$—NH—CO—$(CH_2)_{1-3}$—Z,
—NH—$CH_2$—$CH_2$—(O—$CH_2$—$CH_2)_{1-4}$—Z,
—O—CO—$(CH_2)_{1-13}$—Z, and
—O—CO—CHY—$NH_2$; and HO—CO—CHY—$NH_2$ is a naturally occurring amino acid and Y is the side chain thereof.

Examples of Z radicals are the following radicals: —COOH, —$SO_3H$, —O—$SO_3H$, —P(O)(OH)$_2$, —O—P(O)(OH)$_2$, —O—P(S)(OH)$_2$, —S—P(O)(OH)$_2$ and the salt forms thereof; —$NH_2$, —NHR, —NRR' and the acid addition products thereof; and —$N^+RR'R''X^-$, wherein R, R' and R'', which may be the same or different, are hydrocarbon radicals, preferably alkyl radicals, especially $C_{1-15}$-alkyl radicals, for example $C_{1-5}$-alkyl radicals, and $X^-$ is an anion of a mineral acid or of a carboxylic acid.

It is also possible to use derivatives (a) and/or (b) that have one, two or more C-bonded, preferably terminal, radicals —$S_{0-1}$—Z wherein Z is a radical from the following group: —$NH_2$, —NHR, —NRR' and the acid addition products thereof; —$N^+RR'R''X^-$; and —ConA, —O—ConA and —O—$C_{1-5}$—alkylene-$CO_2H$, especially —O—$C_{1-3}$-alkylene-$CO_2H$; and S—Z is a radical from the following group:
—NH—$(CH_2)_{1-13}$—CO—Z,
—O—$(CH_2)_{1-13}$—CO—Z,
—NH—CO—$(CH_2)_{1-13}$—CO—Z, and
—O—CO—$(CH_2)_{1-13}$—CO—Z, wherein R, R' and R'', which may be the same or different, are hydrocarbon radicals, preferably alkyl radicals, especially $C_{1-15}$-alkyl radicals, for example $C_{1-5}$-alkyl radicals, and $X^-$ is an anion of a mineral acid or of a carboxylic acid.

Con A is Concanavalin A from *Canavalia ensiformis* (Pharmacia Fine Chemicals AB)

In the case of derivatives (a) and/or (b), from 50 to 100%, for example, of the OH groups of the basic polyalkylene glycol or the reaction product of a polyhydric alcohol with an alkylene oxide may be replaced by the groups indicated. Table 1 gives literature references relating to polyalkylene glycol derivatives having some of these radicals.

TABLE 1

| Radical | Literature |
| --- | --- |
| —COOH | Polymer Bulletin, 1 (1979) 691–695 |
| —$SO_3H$ | Biochim. Biophys. Acta, 222 (1970) 381. |
| —O—$SO_3H$ | Report of the Fermentation Research Institute, 52 (1979) 33 |
| —P(O)(OH)$_2$<br>—O—P(O)(OH)$_2$<br>—O—P(S)(OH)$_2$<br>—S—P(O)(OH)$_2$ | German Patent Application P 29 35 134.6 |
| —$NH_2$ | Brandstetter, Diploma thesis, University of Tubingen 1972 |
| —NHR | J. Biol. Chem., 251 (1976) 858 |
| —$\overset{+}{N}RR'R''$ | J. Biol. Chem., 251 (1976) 858<br>Biochim. Biophys. Acta, 222 (1970) 381 |

It is possible to use, for example, derivatives (a) and/or (b) that are derived from polyalkylene glycols or reaction products (polyhydric alcohols with alkylene oxides) having an average molecular weight of from 200 to 40,000, preferably from 500 to 30,000 and especially of from 1000 to 25,000.

It is possible to use, for example, in the process according to the invention derivatives (a) and/or (b), that are derived from polycondensation products of glycol, 1,3-propanediol, 1,2-propanediol or the mixed polycondensation products thereof; or from reaction products of trihydric alcohols, such as glycerine or 2,2-hydroxymethylbutan-1-ol, with alkylene oxides, such as ethylene oxide or propylene oxide.

Examples of polyalkylene glycol derivatives that can be used are compounds of the following general formula:

$$Z-(C_{2-3}-\text{alkylene}-O)_x-C_{2-3}-\text{alkylene-}Z$$

with $Z = -O-P(O)(OH)_2, -P(O)(OH)_2, -O-SO_3H,$
$-SO_3H, -NH_2, -NH(C_{1-15}-\text{alkyl}),$
$-N(C_{1-15}-\text{alkyl})_2, -N^+(C_{1-15}-\text{alkyl})_3 X^-,$
$-O-C_{1-5}-\text{alkylene}-COOH,$
$-NH-CO-C_{1-5}-\text{alkylene}-CO_2H,$
$-O-\text{ConA and/or} -\text{ConA}$ and with an average molecular weight of from 1000 to 25,000, or the salts of the acids, or the acid addition products of the bases, it being possible for one of the Z radicals to be replaced by a $C_{1-5}$-alkoxy or OH group. The following radicals may have the following meanings:

$C_{2-3}$—alkylene = —CH$_2$—CH$_2$—, —CH$_2$—CH$_2$—CH$_2$— or —CH(CH$_3$)—CH$_2$—;
$C_{1-15}$—alkyl = methyl or ethyl; and
$C_{1-5}$—alkylene = —CH$_2$—, —CH$_2$—CH$_2$— or —CH$_2$—CH(CH$_3$)—.

The number of recurring units x is sufficiently large for the average molecular weight of the basic polyalkylene glycol to be in the above-mentioned or indicated range.

Acids may alternatively be used in the form of their lithium, sodium or potassium salts, and bases may alternatively be used in the form of their mineral acid addition products.

Derivatives (a) and (b), which are ion exchangers and dissolve in aqueous multi-phase systems, are known; see, for example, Table 1. Starting from this known state of the art, the man skilled in the art can readily manufacture, in an analogous manner, new derivatives that can be used successfully as ion exchangers in the process according to the invention. In addition, the man skilled in the art can use conventional alkylation and acylation reactions in order to obtain, from commercially available polyethers having functional OH and NH$_2$ groups, derivatives that can be used in the process according to the invention.

The man skilled in the art is familiar with the determination of the activity of interferon; see, for example, Protein, Nucleic Acid and Enzyme, 20 (6) (1975) 616-643 (publishers: K. Shuppan Co., Ltd., Tokyo).

Accompanying protein can be determined, for example, according to M. M. Bradford, Analyt. Biochem., 72 (1976) 248-254. Thus it can be generally stated that the man skilled in the art can, as a matter of routine, determine the partition coefficients for interferon and accompanying protein and select, as a matter of routine, suitable derivatives (a) or (b).

In the process according to the invention, it is possible to use an aqueous multi-phase system, especially an aqueous two-phase system, containing polyether derivative or derivative (a) and/or (b), and
 (i) polysaccharide and/or
 (ii) at least one inorganic or organic salt.

The derivative (a) and/or (b), on the one hand, and the polysaccharide or polysaccharides or the inorganic or organic salt or the inorganic or organic salts, on the other, may be termed phase-forming agents.

Methylcellulose, ethylhydroxyethylcellulose, DEAE-cellulose, alkali metal carboxymethylcellulose, dextran, dextran derivatives, such as hydroxypropyldextran, DEAE-dextran, dextran sulphate and alkali metal carboxymethyldextran, and/or Ficoll may be used as a polysaccharide.

Ficoll = a synthetic polysaccharide, obtained by polymerising cane sugar, average molecular weight approximately 400,000;

dextran = a polysaccharide from glucose, empirical formula $(C_6H_{10}O_5)_x$

Examples of inorganic salts are ammonium and alkali metal salts, preferably salts of mineral acids, such as phosphoric acid and especially potassium phosphate, potassium hydrogen phosphate and/or potassium dihydrogen phosphate.

Examples of organic salts are ammonium and alkali metal salts, preferably salts of carboxylic acids and especially sodium formate and potassium sodium tartrate.

If the process according to the invention is carried out at a pH of from 5 to 8, preferably of from 6.5 to 7.5 and especially of from 6.7 to 7.0, the accompanying proteins have a particularly low partition coefficient. This observation applies especially in the case of interferon obtained from human fibroblasts and an aqueous two-phase system containing bisphosphoric acid polyethylene glycol monoester and potassium phosphate.

Interferon can be separated, for example chromatographically, from polyether derivatives.

The invention is described in more detail below by Examples and one FIGURE.

EXAMPLE 1

Crude interferon with the accompanying protein was partitioned in aqueous two-phase systems. The compositions and the results are given in Tables 2 and 3.

TABLE 2

| Test | System components (Tests 15 to 36 with 1M NaCl. Tests 41 to 122 with 0.5M NaCl; Tests 41 to 43 with 1.5M NaCl) polyethylene glycol derivative (% by wgt.) | dextran 500 000 (% by wgt.) | K$_2$HPO$_4$/ KH$_2$PO$_4$ (% by wgt.) | ethylene glycol (% by wgt.) | pH | partition coefficient interferon | protein |
|---|---|---|---|---|---|---|---|
| 8 | (CH$_3$)$_3$N$^+$—PEG—6000-N$^+$(CH$_3$)$_3$ | 8 | 8 | — | — | 5.0 | 2.21 | 0.28 |
| 9 | " | " | " | — | — | 6.0 | 4.70 | 0.41 |
| 15 | " | " | " | 0.8 | — | 5.4 | 15.2 | 0.04 |
| 16 | " | " | " | " | — | 6.6 | 13.2 | 0.05 |
| 17 | " | " | " | " | — | 7.2 | 36.3 | 0.06 |
| 18 | " | " | " | " | 25 | 4.6 | 49.5 | 0.12 |
| 20 | " | " | " | " | 25 | 6.7 | 5.45 | 0.06 |
| 21 | H$_2$O$_3$P—O—PEG—6000-O—PO$_3$H$_2$ | " | " | " | — | 5.2 | >133 | 0.08 |

TABLE 2-continued

| | | | | | | | | |
|---|---|---|---|---|---|---|---|---|
| 22 | " | " | " | " | — | 6.2 | >109 | 0.05 |
| 23 | " | " | " | " | — | 7.0 | ca.93 | 0.05 |
| 24 | " | " | " | " | 25 | 5.1 | >41 | not det. |
| 25 | " | " | " | " | 25 | 6.1 | >27 | 0.06 |
| 26 | " | " | " | " | 25 | 7.1 | 19.4 | 0.06 |
| 31 | $HO_2C-(CH_2)_2-CO-NH-PEG-6000-NH-CO-(CH_2)_2-CO_2H$ | " | " | " | — | 5.2 | 3.5 | 0.2 |
| 32 | $HO_2C-(CH_2)_2-CO-NH-PEG-6000-NH-CO-(CH_2)_2-CO_2H$ | " | " | " | — | 6.0 | 4.13 | 0.09 |
| 33 | $HO_2C-(CH_2)_2-CO-NH-PEG-6000-NH-CO-(CH_2)_2-CO_2H$ | " | " | " | — | 6.9 | 2.86 | 0.09 |
| 34 | $HO_2C-(CH_2)_2-CO-NH-PEG-6000-NH-CO-(CH_2)_2-CO_2H$ | " | " | " | 25 | 5.2 | 11.7 | 0.32 |
| 35 | $HO_2C-(CH_2)_2-CO-NH-PEG-6000-NH-CO-(CH_2)_2-CO_2H$ | " | " | " | 25 | 6.2 | 13.5 | 0.10 |
| 36 | $HO_2C-(CH_2)_2-CO-NH-PEG-6000-NH-CO-(CH_2)_2-CO_2H$ | " | " | " | 25 | 6.6 | 30.2 | 0.09 |
| 41 | $C_8H_{17}-\overset{+}{N}H_2-PEG-6000-\overset{+}{N}H_2-C_8H_{17}$ | " | " | " | — | 5 | 4.8 | 8.3 | not det. |
| 42 | " | " | " | " | — | 12 | 4.8 | 20.7 | not det. |
| 43 | " | " | " | " | — | 30 | 4.8 | 11.9 | not det. |

| Test | System components (with 0.5M NaCl in all cases) polyethylene glycol derivative (% by weight) | dextran-500000 (% by wgt.) | $K_2HPO_4$/$KH_2PO_4$ (% by wgt.) | ethylene glycol (% by wgt.) | pH | Partition coefficient inter-feron | pro-tein[a] |
|---|---|---|---|---|---|---|---|
| 56 | $(CH_3)_3N^+-PEG-5000-OCH_3$ | 8 | 8 | 0.8 | — | 6 | 1.5 | 0.010 |
| 57 | " | " | " | " | — | 7 | 3.8 | 0.011 |
| 59 | " | " | " | " | 30 | 5 | 3.8 | ca.0.19 |
| 60 | " | " | " | " | — | 6 | 4.1 | 0.019 |
| 61 | " | " | " | " | — | 7 | ca.13 | 0.033 |
| 63 | $NH_2-PEG-6000-NH_2$ | " | " | " | — | 5 | 4.5 | 0.035 |
| 64 | " | " | " | " | — | 6 | 2.2 | 0.020 |
| 65 | " | " | " | " | — | 7 | 2.3 | 0.041 |
| 80 | Cibacron Blue—NH—$(CH_2)_6$—NH—PEG—6000-NH—$(CH_2)_6$—NH—Cibacron Blue | " | " | " | — | 6 | $0^b$ | $0.13^c$ |
| 84 | Cibacron Blue—NH—$(CH_2)_6$—NH—PEG—6000-NH—$(CH_2)_6$—NH—Cibacron Blue | " | " | " | 30 | 6 | $0^b$ | not det. |
| 88 | Cibacron Blue—NH—PEG—6000-NH—Cibacron Blue | " | " | " | — | 6 | ≧1 | $0.30^c$ |
| 91 | Cibacron Blue—NH—PEG—6000-NH—Cibacron Blue | " | " | " | 30 | 6 | $0^b$ | $0.28^c$ |
| 96 | ConA—O— or ConA—PEG—6000-ConA or —O—ConA | " | " | " | — | 6 | 37 | $0.05^d$ |
| 97 | ConA—O— or ConA—PEG—6000-ConA or —O—ConA | " | " | " | — | 7 | 27 | $0.05^d$ |
| 99 | ConA—O— or ConA—PEG—6000-ConA or —O—ConA | " | " | " | 30 | 5 | 28 | $0.05^d$ |
| 100 | ConA—O— or ConA—PEG—6000-ConA or —O—ConA | " | " | " | — | 6 | 36 | $0.05^d$ |
| 104 | $(CH_3)_3N^+-PEG-1550-N^+(CH_3)_3$ | 9.4 | 7.8 | 0.78 | — | 6 | 2.1 | 0.74 |
| 105 | " | " | " | " | — | 7 | 3.1 | 0.36 |
| 108 | " | " | " | " | 30 | 6 | 3.3 | 0.42 |
| 109 | " | " | " | " | — | 7 | 6.7 | 0.43 |
| 133 | $H_2O_3P-O-PEG-6000-O-PO_3H_2$ | 14 | — | 14 | — | 6.7 | 170 | 0.04 |
| $132^f$ | " | 1 | — | 19.5 | — | 6.7 | ≧169 to 321 | 0.23 to 0.35 |
| 144, 146, 150, 152 and 155 with the same system composition[f] 122, 146, 150, 152 and 155 with the same system composition[f] | | 1 | — | 19.5 | — | 6.7 | 345 | not det. |

Key:
[a] determination with Coomassie Brilliant Blue
[b] Cibacron Blue possibly binds interferon under the test conditions so that the K value is falsified
[c] immunological protein determination
[d] estimated by means of disc gels
[f] interferon that has been subjected to coarse purification by precipitation with perchloric acid; in addition, crude interferon, i.e. manufacture medium, was used that had not been subjected to a purification step except for the optional separation of insoluble material
PEG = polyethylene glycol having the indicated terminal functional groups; the Arabic numeral indicates the average PEG molecular weight.

The exact degree of substitution of the individual polyethylene glycol derivatives was not known ConA = Concanavalin A from *Canavalia ensiformis* (Pharmacia Fine Chemicals AB)

Cibacron Blue=Reactive Blue 2 (Colour Index 61 211)

Coomassie Brilliant Blue=Acid Blue 90 (Colour Index 42 655).

absorbed (spot test). The interferon was eluted only by a gradient of up to 50% ethylene glycol (or 60% propylene glycol) and 1 M NaCl (all in 0.02 M sodium phosphate buffer, pH=3).

TABLE 3

| | starting material | | product upper phase (in each case a total of ca. 255 g) | | | yield (upper phase) | | |
|---|---|---|---|---|---|---|---|---|
| Test | quantity (mg) | interferon units | vol. (ml) | (units/ml) | protein conc. (mg/ml) | lower phase (units/ml) | total units | (%) | specific activity (units/mg) |
| 144 | 83.7 | 803 000 | 8.6 | 88 000 ±$^d$ 35 000 | 0.012 | | 757 000 | 94.2 | 7.3 × 10$^6$ |
| 146 | 98.7 | 943 000 | 8.2 | 85 000 ±$^d$ 31 000 | 0.017 | | 697 000 | 73.9 | 5.0 × 10$^6$ |
| 150 | 90.0 | 864 000 | 8.3 | 82 000 ±$^d$ 27 000 | 0.027 | ≦400 | 681 000 | 78.8 | 3.0 × 10$^6$ |
| 152 | 106.8 | 1 025 000 | 8.4 | 100 000 ±$^d$ 25 000 | 0.022 | | 840 000 | 81.9 | 4.5 × 10$^6$ |
| 155 | 93.6 | 898 000 | 8.7 | 121 000 ±$^d$ 18 000 | 0.017 | 714 ± 277 | 1 050 000 >100 | | 7.1 × 10$^6$ |

Key:
$^d$parallel titrations in one day

In the case of partition coefficients of $10 \leq K \leq 50$ practically any volume ratio of upper phase to lower phase is suitable for interferon concentration. However, since interferon passes practically quantitatively into the upper phase, small volume ratios offer the advantages that interferon can be obtained in concentrated form in the upper phase and only a small quantity of polyalkylene glycol derivative is required; these facts are illustrated in Table 4 by a comparison of Tests 133 and 132.

TABLE 4

| test | upper phase (ml) | lower phase (ml) | volume ratio upper phase: lower phase | H$_2$O$_3$P—O—PEG—6000-—O—PO$_3$H$_2$ (% by weight) |
|---|---|---|---|---|
| 133 | 1.7 | 2.6 | 0.65 | 14 |
| 132 | 6.5 | 257 | 0.025 | 1 |

EXAMPLE 2 (FIG. 1)

An aqueous two-phase system was manufactured having 12% by weight of bisphosphoric acid polyethylene glycol monoester (average PEG molecular weight 6,000, degree of substitution 1.2 titrated), 12% by weight of potassium phosphate and 0.5 M NaCl. The partition coefficient of the proteins accompanying the crude interferon was determined in dependence on the pH value. The results obtained are shown in the chart in FIG. 1. The most favourable result for interferon purification was obtained at a pH of approximately 6.8.

EXAMPLE 3

In Test 122 (Example 1) the upper phase of the two-phase system was worked up in the following manner. The upper phase was separated from the lower phase and diluted with two parts water. Chromatography was then carried out in the usual manner over Blue Sepharose Cl-6B (Pharmacia). It was also possible to use columns equilibrated with 0.02 M sodium phosphate buffer and 0.15 M sodium chloride at pH 3. Unlike the interferon, the polyethylene glycol derivative was not

EXAMPLE 4

As an alternative, it was possible to carry out the working up in Test 122 as follows. In this case too, the upper phase was separated off and diluted with two parts water. Chromatography was then carried out over ConA-Sepharose columns that had been equilibrated with 0.02 M sodium phosphate buffer at pH 7.4. These columns did not bind the ethylene glycol derivative appreciably, while interferon was eluted only in the presence of 0.1 M α-methyl-D-mannoside and 1 M NaCl by a gradient of up to 50% ethylene glycol (all in 0.02 M sodium phosphate buffer, pH=7.4).

There follows an explanation of phosphorous-containing polyether derivatives and of their manufacture in greater detail, i.e. of compounds of the general formula

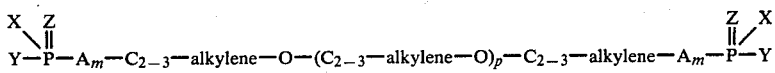

wherein
p=1 to 800 and
(a1)
m=1,
A=an oxygen atom,
X=a chlorine atom or a hydroxyl group,
Y=X or an alkoxy radical having 1 to 5 carbon atoms,
Z=an oxygen or sulphur atom; or
(a2)
m=1,
A=an oxygen atom,
X=an alkoxy radical having 1 to 5 carbon atoms, a phenylalkoxy radical having 0 to 5 carbon atoms in the alkylene group, an alkylamino radical having 1 to 5 carbon atoms, a dialkylamino radical having 1 to 5 carbon atoms in each of the alkyl groups, a phenylalkylamino radical having 0 to 5 carbon atoms in the alkylene group, a bisphenylalkylamino radical having 0 to 5 carbon atoms in each of the alkylene groups, or a p-nitrophenoxy radical, it being possible for the phenyl groups of the phenylalkoxy radicals, phenylalkylamino radicals and bisphenylalkylamino radicals to be substituted by a hydroxyl radical, by an alkyl radical having 1 to 5 carbon atoms or by an alkoxy radical having 1 to 5 carbon atoms, Y=X or an alkoxy radical having 1 to 5 carbon atoms, and Z=an oxygen atom; or (a3)
m=1,
A=an oxygen atom,
X=a hydroxyl radical,
Y=an alkylthio radical having 1 to 5 carbon atoms, an aminoalkylthio radical having 2 to 5 carbon atoms or a carboxyalkylthio radical having 1 to 5 carbon atoms in the alkylene group, and
Z=an oxygen atom; or (b)
m=1,
A=a sulphur atom,
X=Y=a hydroxyl radical and
Z=an oxygen atom; or (c)
m=0,
X=Y=a hydroxyl radical, an alkoxy radical having 1 to 5 carbon atoms, a phenylalkoxy radical having 0 to 5 carbon atoms in the alkylene group, it being possible for the phenyl group to be substituted by a hydroxyl radical, by an alkyl radical having 1 to 5 carbon atoms or by an alkoxy radical having 1 to 5 carbon atoms, or a trialkylsilyloxy radical having 1 to 5 carbon atoms in the alkyl groups, and
Z=an oxygen atom,
and their derivatives in which one of the two

groups is replaced by an alkoxy group having 1 to 5 carbon atoms, and the alkali metal salts and salts with ammonia and with amines, of the acids of phosphorus and of the carboxylic acids.

The polyether chain of the above compounds is made up of ethylene glycol, propylene glycol or i-propylene glycol units or of more than one of these units; in this case p can have a value of 3 to 250 and preferably of 30 to 160.

Examples of alkoxy radicals are the methoxy, ethoxy and propoxy radicals. Examples of optionally nuclear-substituted phenylalkoxy radicals are optionally nuclear-substituted alkoxy radicals having 0 or 1 carbon atom in the alkylene group. Examples of alkylamino and dialkylamino radicals are the methylamino, ethylamino and propylamino radicals and the dimethylamino, diethylamino and dipropylamino radicals, respectively. Examples of optionally nuclear-substituted phenylalkylamino and bisphenylalkylamino radicals are optionally nuclear-substituted phenylalkylamino and bisphenylalkylamino radicals, respectively, having 0 or 1 carbon atom in the alkylene group. Examples of alkylthio radicals are alkylthio radicals having 1 to 3 carbon atoms. Examples of aminoalkylthio radicals are aminoalkylthio radicals having 2 or 3 carbon atoms. Examples of carboxyalkylthio radicals are carboxyalkylthio radicals having 1 to 3 carbon atoms in the alkylene group. An example of a trialkylsilyloxy radical is the trimethylsilyloxy radical.

The nuclear substituents of the nuclear-substituted phenylalkoxy, phenylalkylamino and bisphenylalkylamino radicals may be methyl, ethyl, propyl, methoxy, ethoxy and/or propoxy radicals.

The salts are preferably salts of the acids of phosphorus, preferably ammonium, lithium, sodium or potassium salts.

Polyethylene glycol, polypropylene glycol, poly-i-propylene glycol or their copolymers may be used as starting materials for the manufacture of all the compounds. Methods of manufacture are described below.

(I) Manufacture of compounds of the general formula wherein m=1; A=an oxygen atom; X=a chlorine atom or a hydroxyl radical; Y=X or an alkoxy radical having 1 to 5 carbon atoms; Z=an oxygen atom For the manufacture of phosphoric acid halides, a polyethylene glycol can be reacted with phosphorus oxychloride or pyrophosphoryl chloride with or without a solvent, such as a phosphoric acid trialkyl ester, for example triethyl phosphate, or dichloromethane, in the presence of an acid-binding agent, for example a tertiary base, such as triethylamine or pyridine, or in the presence of a molecular sieve (of, for example, 0.4 nm). The phosphoric acid halides obtained can be hydrolysed with water or firstly with half the stoichiometric quantity of a $C_{1-5}$-alcohol and then with water to form the free phosphoric acids.

The free phosphoric acids can also be obtained directly by reacting with a mixture of phosphorus pentoxide and 85% phosphoric acid (condensed phosphoric acids) in the molten state. The reaction mixture can be worked up by hydrolysis and recrystallisation from absolute ethanol.

(II) Manufacture of compounds of the general formula wherein m=1; A=an oxygen atom; X=Y=a chlorine atom or a hydroxyl radical; Z=a sulphur atom Such compounds are obtained by reacting, for example, a polyalkylene glycol with thiophosphoryl chloride in a solvent, for example in a phosphoric acid trialkyl ester, such as triethyl phosphate. The halide obtained can be saponified, for example at a pH of approximately 7 in the presence of lithium hydroxide. The free acid can be liberated from the lithium salt in the usual manner.

(III) Manufacture of compounds of the general formula wherein m=1; A=an oxygen atom; X=Y=an alkoxy radical having 1 to 5 carbon atoms, an optionally nuclear-substituted phenylalkoxy radical having 0 to 5 carbon atoms in the alkylene group, an alkylamino or dialkylamino radical having 1 to 5 carbon atoms in the alkyl radical, an optionally nuclear-substituted phenylalkylamino or bisphenylalkylamino radical having 0 to 5 carbon atoms in the alkylene group, a p-nitrophenoxy radical; Z=an oxygen atom The esters can be obtained either by esterifying in the usual manner the free phosphoric acids obtained according to (I) or directly by reacting with alcohols the phosphoric acid halides obtained according to (I). If the phosphoric acid halides obtained according to (I) are reacted with amines the phosphoric acid amides are obtained.

(IV) Manufacture of compounds of the general formula wherein m=1; A=an oxygen atom; X=a hydroxyl radical; Y=an alkylthio radical having 1 to 5 carbon atoms, an aminoalkylthio radical having 2 to 5 carbon atoms, a carboxyalkylthio radical having 1 to 5 carbon atoms in the alkylene group; Z=an oxygen atom The compounds with alkylthio radicals can be obtained, for example, by reacting the compounds obtained according to (II) and having terminal (LiO)$_2$P(S)—O— radicals, with a trialkyl phosphate in an aqueous medium. By reacting the mentioned compounds obtained according to (II) with an aminoalkyl halide having 2 to 5 carbon atoms or with its hydrohalide, the compounds having aminoalkylthio radicals are obtained. For example, it is possible to use an ω-bromoalkylamine or its hydrobromide. Accordingly, by reaction with a halocarboxylic acid having 1 to 5 carbon atoms in the alkylene chain, for example bromoacetic acid, the compounds having carboxyalkylthio radicals are obtained. In all three cases, therefore, the (LiO)$_2$P(S)—O— radical is alkylated at the sulphur atom.

(V) Manufacture of compounds of the general formula wherein m=1; A=a sulphur atom; X=Y=a hydroxyl radical; Z=an oxygen atom For the manufacture of such compounds, a polyalkylene glycol can be reacted with a thionyl halide, for example thionyl bromide, in a solvent in the presence of an amine, for example in toluene in the presence of triethylamine. The resulting dihalide having terminal halogen atoms can be reacted in an Åkerfeldt reaction to form compounds having (O$^-$)$_2$P(O)—S— radicals, for example with (LiO)$_3$PS in a water/DMF mixture. The free acid can be obtained in known manner from the resulting compound.

(VI) Manufacture of compounds of the general formula wherein m=0; X=Y=a hydroxyl radical, an alkoxy radical having 1 to 5 carbon atoms, an optionally nuclear-substituted phenylalkoxy radical having 0 to 5 carbon atoms in the alkylene group, a trialkylsilyloxy radical having 1 to 5 carbon atoms in the alkyl groups; Z=an oxygen atom For the manufacture of such compounds a polyether obtained according to (V) and having terminal halogen atoms can be subjected to a Michaelis-Arbusov reaction and reacted with a trialkyl phosphite to form phosphonic acid esters. Such esters can also be obtained by means of a Michaelis-Becker reaction in which a polyether having terminal halogen atoms is reacted with alkali metal phosphorous acid dialkyl esters, for example sodium phosphorous acid dialkyl esters, in a solvent, such as benzene, toluene or an alcohol. The esters obtained can be saponified directly with acids, for example concentrated hydrochloric acid, to form the free phosphonic acids. The free phosphonic acids can, however, also be obtained firstly by reacting the phosphonic acid esters with a trialkylsilyl halide, for example with trimethylsilyl chloride or bromide, and then saponifying with water. This method of saponification is milder than saponification by means of acids. In the Michaelis-Arbusov reaction an optionally nuclear-substituted triphenyl phosphite may be used instead of trialkyl phosphite.

(VII) Manufacture of compounds of the general formula, in which compounds one of the two YXP(Z)—O— groups is replaced by an alkoxy group having 1 to 5 carbon atoms Such compounds are obtained by using polyalkylene glycols in which one of the terminal OH radicals is etherified by a C$_{1-5}$-alkyl group as starting materials.

(VIII) Manufacture of salts of carboxylic acids and acids of phosphorus from compounds of the general formula Insofar as such salts have not already been discussed above they are obtained by customary neutralisation.

We claim:

1. A process for the purification of interferon consisting essentially of (1) partitioning interferon in an aqueous multi-phase system in the presence of at least one ion exchanger which is soluble in said system selected from the group consisting of (a) polyoxyalkylene glycols and (b) reaction products of polyhydric alcohols with alkylene oxides, which ion exchanger contains at least one carbon-bound group —S$_{0-1}$—Z, wherein —S—Z is a member selected from the group consisting of:

—NH—(CH$_2$)$_{1-14}$—Z,
—O—(CH$_2$)$_{1-14}$—Z,
—NH—CO—(CH$_2$)$_{1-14}$—Z,
—NH—(CH$_2$)$_{1-14}$—NH—CO—(CH$_2$)$_{1-3}$—Z,
—NH—CH$_2$—CH$_2$—(O—CH$_2$—CH$_2$)$_{1-4}$—Z and
—O—CO—(CH$_2$)$_{1-13}$—Z and —Z is a member selected from the group consisting of:

—P(O)(OH)$_2$,
—O—P(O)(OH)$_2$,
—O—P(S)(OH)$_2$,
—S—P(O)(OH)$_2$ and their salt forms, (2) separating the phases including an interferon containing phase and (3) recovering purified interferon from said interferon containing phase.

2. The process of claim 1 wherein the at least one ion exchanger has at least one terminal —S$_{0-1}$—Z group.

3. The process of claim 1 wherein said polyoxyalkylene glycols are polycondensation products of ethylene glycol, 1,3-propanediol, 1,2-propanediol and mixtures thereof, and said reaction products of polyhydric alcohols with alkylene oxides are reaction products of trihydric alcohols with alkylene oxides.

4. The process of claim 3 wherein said trihydric alcohols are selected from the group consisting of glycerine and 2,2-hydroxymethylbutan-1-ol and said alkylene oxides are selected from the group consisting of ethylene oxide and propylene oxide.

5. The process of claim 3 wherein said polycondensation products and said reaction products of trihydric alcohols with alkylene oxides have an average molecular weight of from 200 to 40,000.

6. The process of claim 5 wherein said average molecular weight is from 500 to 30,000.

7. The process of claim 6 wherein said average molecular weight is from 1000 to 25,000.

8. The process of claim 3 wherein said polycondensation products are employed as said at least one ion exchanger and have the formula:

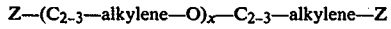

Z—(C$_{2-3}$—alkylene—O)$_x$—C$_{2-3}$—alkylene—Z wherein Z is a member selected from the group consisting of:

—P(O)(OH)$_2$
—O—P(O)(OH)$_2$
—O—P(S)(OH)$_2$
—S—P(O)(OH)$_2$ and their salt forms, where one of said Z groups may be replaced by a C$_{1-5}$-alkoxy or an OH, said polycondensation products having a value for x sufficient to give an average molecular weight of from 1,000 to 25,000.

9. The process of claim 1 or 2 or 3 or 4 or 5 or 6 or 7 or 8 wherein —Z is in its salt form, said salt being selected from the group consisting of lithium, sodium and potassium.

10. The process of claim 1 or 2 wherein said aqueous multi-phase system is a two phase system and further contains a phase-forming agent selected from the group consisting of (A) polysaccharides, (B) at least one inorganic or organic salt, and (C) mixtures thereof.

11. The process of claim 10 wherein said polysaccharides are members selected from the group consisting of methylcellulose, ethylhydroxyethylcellulose, DEAE-cellulose, alkali metal carboxymethylcellulose, dextran, modified dextran, hydroxypropyldextran, DEAE-dextran, dextran sulfate, alkali metal carboxymethyldextran and Ficoll.

12. The process of claim 10 wherein said inorganic or organic salt is a member selected from the group consisting of ammonium and alkali metal salts of mineral acids and carboxylic acids.

13. The process of claim 10 wherein said inorganic or organic salt is a member selected from the group consisting of alkali metal and ammonium phosphates, formates and tartarates.

14. The process of claim 1 wherein said aqueous multi-phase system is maintained at a pH of from 5 to 8.

15. The process of claim 1 wherein said aqueous multi-phase system is maintained at a pH of from 6.5 to 7.5.

16. The process of claim 1 wherein said aqueous multi-phase system is maintained at a pH of from 6.7 to 7.0.

* * * * *